United States Patent [19]

Küsebauch et al.

[11] 4,445,091
[45] Apr. 24, 1984

[54] METHOD FOR DETERMINING THE PH VALUE OF DEIONIZED WATER

[75] Inventors: Walter Küsebauch, Erlangen; Theodor Renner, Nuremberg, both of Fed. Rep. of Germany

[73] Assignee: Siemens Aktiengesellschaft, Munich, Fed. Rep. of Germany

[21] Appl. No.: 279,201

[22] Filed: Jun. 30, 1981

[30] Foreign Application Priority Data

Jul. 18, 1980 [DE] Fed. Rep. of Germany ....... 3027306

[51] Int. Cl.³ .............................................. G01N 27/56
[52] U.S. Cl. .................................... 324/438; 324/439
[58] Field of Search ................ 324/438, 439; 210/662

[56] References Cited

U.S. PATENT DOCUMENTS 3,681,025  8/1972  Dalgaard ............................ 324/438
3,904,365  9/1975  Larson et al. ...................... 324/439

OTHER PUBLICATIONS

"Chemistry Pocket Crammer", Manfred Low, Key Publishing Co., Inc., New York, 1963, p. 122.
VGB Kraftwerktechnik 59, Nov. 1979-pp. 885-889.

Primary Examiner—Michael J. Tokar
Assistant Examiner—Kevin D. O'Shea
Attorney, Agent, or Firm—Kenyon & Kenyon

[57] ABSTRACT

A method for determining the pH value of deionized cooling water in a system with a main loop and at least one parallel loop in which the electric conductivity of the cooling water in the main loop and the electric conductivity of the cooling water in the parallel loop behind an ion exchanger is measured and the $H^+$ ion concentration is derived therefrom.

8 Claims, 2 Drawing Figures

METHOD FOR DETERMINING THE PH VALUE OF DEIONIZED WATER

The invention relates to a method for determining the pH value of deionized water in a system comprising a main loop and at least one parallel loop.

For cooling electrical devices of large power rating, for instance, generator and travelling field tubes as well as heavy duty cables, as is well known, closed cooling systems, which contain deionized cooling water, so-called deionate are provided. The cooling water flows through the current carrying conductors of the device, which in general consist of copper or copper alloys. It is also well known to provide secondary loops, which can also be implemented as closed cooling loops and can be provided with a mixed-bed filter, for cooling of particularly sensitive cooling points, for instance, cooling heads and seals of boiler circulating and boiler feed pumps in power generating stations. It is further known that the water steam loop of thermal power generating stations contains deionized water.

In order to keep the electrolyte content in the cooling system as low as possible, a small substream of the cooling water, which may amount to, for instance, about 0.5 to 5%, can be conducted via a parallel loop which contains the mixed-bed filter. In such cooling systems, the cooling water is made to have very low electric conductivity which may be less than 1 uS/cm. The cooling water can remove part of the copper or the copper alloy by corrosion and deposit it again at other points or in following parts of the system. The corrosion removal rate depends on the pH value of the cooling water and assumes a minimum for a predetermined pH value. The pH value of the cooling water is therefore an important variable for the corrosion of metals.

The electric conductivity of the water can be measured by means of conductivity measuring cells. The intrinsic dissociation of the water leads to an electric conductivity of only 0.064 $\mu$S/m at a temperature of 298 K. This low conductivity of the desalinated water is the cause of difficulty in pH measurement with glass electrodes. Absorption of carbon dioxide changes the pH value if air gets into the cooling water during the sampling. In addition, the diaphragm glass of the glass electrodes generally used in pH measuring devices is hydrolyzed, giving off alkali metals. The diffusion voltage at the reference electrode can also have a disturbing effect on the pH measurement. The diffusion voltage comes about because of the differences between the migration velocities of the ions which participate in the electrolytic conduction between the reference electrode and the measurement solution. In desalinated water, these diffusion voltages are not always reproducible and furthermore depend on the flow. In addition, the dissociation constant of water and therefore also the pH value at the neutral point are temperature dependent. The determination of the pH value with a so-called stationery pH measuring chain therefore requires a relatively large amount of equipment (VGB Kraftwerkstechnik 59, Nov. 1979, pages 885 to 889).

It is an object of the present invention to describe a method with which the pH value of deionized water in a system can be determined in a simple manner to a very good approximation by measuring the electric conductivity.

SUMMARY OF THE INVENTION

According to the present invention, this problem is solved in a method for determining the pH value of deionized cooling water in a system with a main loop and at least one parallel loop in which the electric conductivity of the cooling water in the main loop and the electric conductivity of the cooling water in the parallel loop behind an ion exchanger is measured and the H+ ion concentration is derived therefrom. The conductivity $x_1$ in the main loop is due to cations and anions which can be divided into two groups. In the basic region, the alkali ions and metal ions belong to the first group such as copper, iron and nickel ions, in which the OH− anion is present as a partner. To the second group belong all cations which have another ion as a partner such as $HCO_3^-$, $CO_3^=$, $SO_4^=$, as well as Cl− ions. The conductivity $x_1$ in the main loop can therefore be divided into the conductivity components of the two groups.

If this water flows in the parallel loop through an ion exchanger, which is a cation exchanger in the pH range above 7, then the cations of the first group are exchanged for the H+ ions, and additional water is formed. The cations of the second group are likewise exchanged for H+ ions but they contribute, like the corresponding anions, to the conductivity. At low concentration, complete dissociation can be assumed, and with a degree of dissociation approximately equal to 1, the conductivity $x_2$ in the parallel loop is obtained from the charge number, the mobility and the concentration of the ions. The limits of the ion mobility in aqueous solution are known. Since the conductivity of the cations and the anions are proportional to their mobilities, the conductivity of the OH− ions can be calculated with very good approximation, and one then obtains the pH value as the negative logarithm of the H+ ion concentration.

The ion exchanger is a cation exchanger for pH value determination in basic water with pH values above 7, and an anion exchanger for pH value determinations in acid water with pH values below 7. It has a high degree of purity. In the embodiment using a cation exchanger, which may preferably contain a strongly acid resin in H form, it retains the cations and gives off no anions and also no acid radicals or other impurities. In the embodiment using an anion exchanger, which may preferably contain a strongly basic resin in OH form, it filters out the anions and gives off no cations and no base radicals or other impurities.

If the pH value is to be determined in a system with water low in ions, which may be basic as well as acid, preferably two parallel loops, each with an ion exchanger and a conductivity measuring cell in series, may be provided. One of the parallel loops then contains a cation exchanger, and the other one an anion exchanger. The electric conductivity $x_3$ behind the anion exchanger then serves, in conjunction with the conductivity $x_1$ in the main loop, for determining the pH value in the acid range. By addition of an alkalizer or an acid in the main loop and the corresponding change of the conductivity $x_3$ the pH value range of the water is determined.

At the measuring points of the system, at which the conductivity is measured, the water temperature can also, preferably, be measured, which can be taken into consideration in determining the pH value.

DETAILED DESCRIPTION

Figure 1:
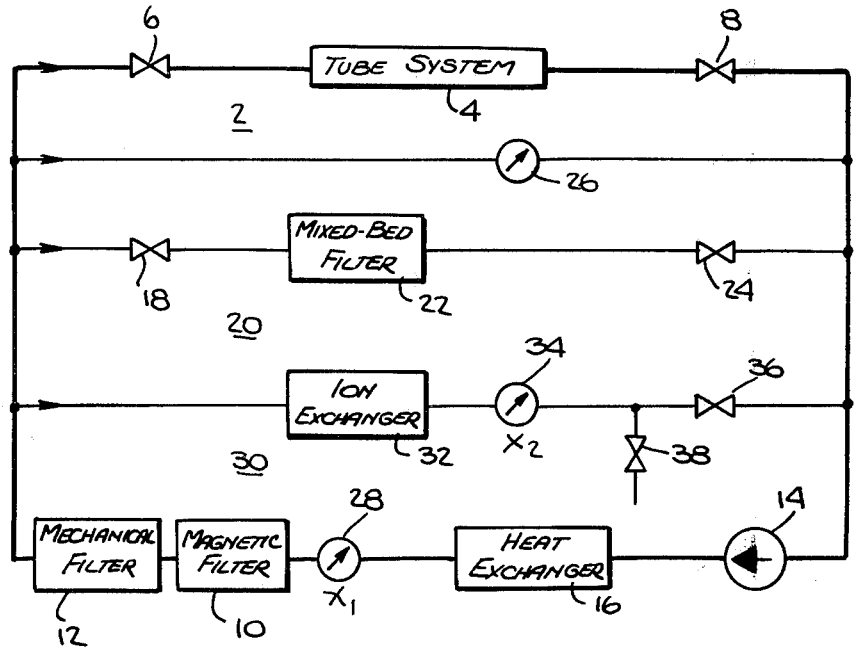
FIG. 1 is a schematic representation of an embodiment of a cooling system with a pH value, the range of which is known.

According to FIG. 1, the tube system 4 of an electrical device, for instance, a water cooled generator winding, is arranged in the main loop 2 in series with two valves 6 and 8, as well as a magnetic filter 10, a mechanical filter 12 and a circulating pump 14. Heat in the generator winding is absorbed by the cooling water, and is fed to a heat exchanger 16 which gives off the transferred heat, for instance, to the water of a river. In a parallel loop 20, in series with two valves 18 and 24, a mixed-bed filter 22 is provided. Filter 32 filters out from the cooling water the metal ions, for instance, copper, nickel and iron ions as well as $HCO_3^-$ and $CO_3^=$ ions and reduces the electric conductivity to very low values, for instance, 0.1 uS/cm. In a further parallel loop, an oxygen measuring device 26 may advantageously be provided in addition.

The pH value is determined by means of the conductivity measuring cell 28 which is arranged for measuring the electric conductivity $x_1$ in the main loop 2, and a further conductivity measuring cell 34 which is arranged in a parallel loop 30 behind an ion exchanger 32, which is a cation exchanger for determining pH values in the range above 7. The parallel loop 30 can be shut off by throttling valve 36 and that part of the water which has flowed through the cation exchanger 32 and, except for H+ ions, is substantially free of cations, can be taken from the system via a valve 38. A substream of the cooling water is conducted via the hydrogen charged cation exchanger 32 in the parallel loop 30, and the conductivity $x_2$ in this parallel loop is measured with the conductivity measuring cell 34.

The conductivity in the main loop is due to cations and anions which can be divided into two groups. To the first group belong the Na+ ions and metal ions such as copper, iron and nickel ions, for which the OH− anion is present as a partner. To the second group belong all cations which have another anion as a partner, for instance, $HCO_3^-$, $CO_3^=$ and $SO_4^=$ as well as $Cl^-$ ions.

The conductivity $x_1$ of the water in the main loop can therefore be divided into the conductivity components of the first group, i.e., the conductivity component $x_{K1}$ of the alkali ions and metal ions, and the conductivity component $x_{OH}$ of the corresponding OH ions, and the conductivity components of the second group, mainly the conductivity component $x_{K2}$ of the cations of the second group and the conductivity component $x_A$ of the corresponding anions. In addition, the intrinsic dissociation of the water contributes to the conductivity with a conductivity component.

The conductivities of the cations and the anions are proportional to their mobilities because the concentration of the cations is equal to the concentration of the anions. Furthermore, complete dissociation can be assumed at low concentrations. One can therefore calculate the individual conductivity components from the ion mobilities $l_H$ of the H ions, $l_{OH-}$ of the OH ions, $l_K$ of the cations as well as $l_A$ of the anions, and the conductivity $x_2$, and the conductivity component $x_{OH}$ is obtained from the relation $$x_1 = \left(\frac{l_K}{l_{OH}} + 1\right) \cdot x_{OH} + \frac{l_K + l_A}{l_A + l_H} \cdot x_2$$

$$x_{OH} = \frac{x_1 - \frac{l_K + l_A}{l_A + l_H} \cdot x_2}{\frac{l_K}{l_{OH}} + 1}$$

By means of the ion product $K_w$ of the water and the definition of the pH value as the negative logarithm of the H+ ion concentration one obtains the pH value $$pH = -\log \frac{(l_K + l_{OH})K_w}{1000} + \log\left(x_1 - \frac{l_K + l_A}{l_A + l_H} \cdot x_2\right)$$

The mobility of the ions and the ion product $K_w$ of the water and the conductivities are temperature dependent. This temperature dependence is known. The temperature is measured at the conductivity measuring cells and can preferably be kept, at least approximately, at the same value. For a temperature of, for instance, 298 K one obtains with a mean cation mobility, for instance, of the Na+ ions, Cu+, Fe++ and Ni++ ions, of 52 ohm$^{-1}$ cm$^2$ and with a mean anion mobility, for instance, of the $HCO_3^-$, $CO_3^=$, $SO_4^=$, $Cl^-$ ions, of 62 ohm$^{-1}$ cm$^2$, and with a mobility of the $H^{30}$ ions $l_H = 349.8$ ohm cm$^2$ and a mobility of the OH− ions $l_{OH} = 198.6$ ohm $^{-1}$ cm$^2$ as well as the ion product of the water $K_w = 1.008$ times $10^{-14}$ the pH value from the relation $$pH = 14.60 + \log(X_1 - 0.2768 X_2)$$

The deviation of the resulting pH value from the actual pH value is less than 1%, for instance, for pH values above 8.1.

For determining the pH value in the acid region, an anion exchanger is chosen as the ion exchanger 32. Behind the anion exchanger, a different electric conductivity $x_4$ is measured and one obtains the pH value in the region below 7 by corresponding derivation in good approximation from the relation $$pH = +\log \frac{l_H + l_A}{1000} - \log\left(x_1 - \frac{l_K + l_A}{l_K + l_{OH}} \cdot X_4\right)$$

For a temperature of, for instance, 298 K at the measuring points of the electric conductivity, the pH value is obtained from the simplified relation $$pH = -0.3853 - \log(x_1 - 0.4549 x_4)$$

The deviation of the resulting pH value from the actual pH value is substantially less than 1% in the acid region, for instance, for pH values below 6.1.

Figure 2:
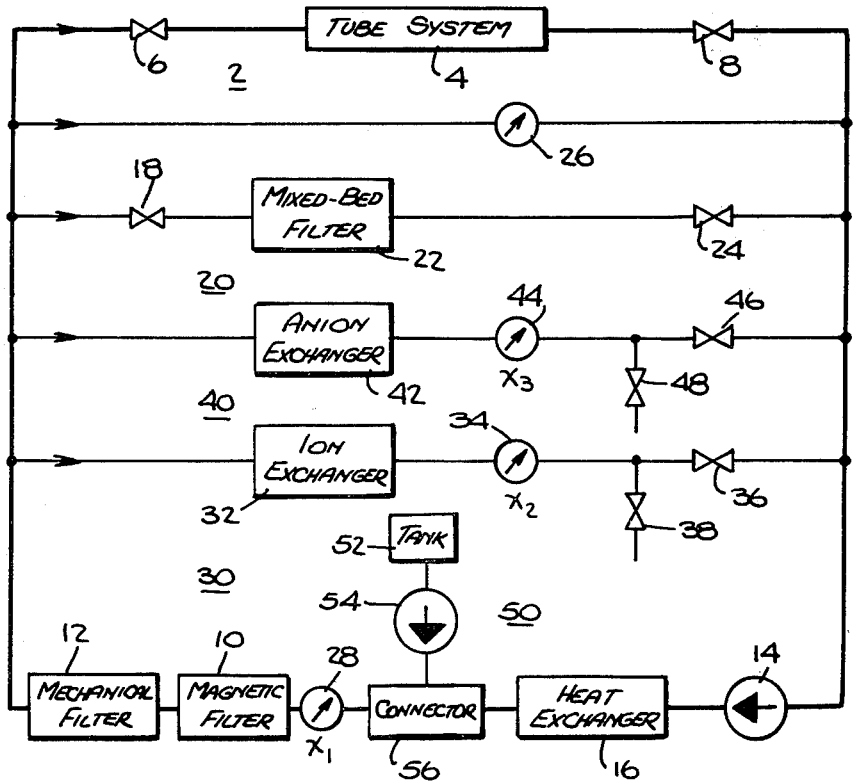
FIG. 2 illustrates an arrangement cooled with deionized cooling water, the pH value of which is higher or lower than 7 and is to be measured with the method according to the invention.

If it is not known whether the deionized water, the pH value of which is to be determined, is in the basic pH value range above 7 or in the acid pH value range below 7, a pH value determination can be made with the arrangement according to FIG. 2, in which parts corresponding to FIG. 1 are provided with the same reference numerals. The system is likewise to be provided for cooling a generator winding, the cooling tube system 4 of which, together with a magnetic filter 10, a mechanical filter 12 and a circulating pump 14 as well as with a heat exchanger 16 is arranged in the main loop 2. The arrangement contains in the parallel loop 20 a mixed-bed filter 22 in series with the valves 18 and 24. The parallel loop 30 which serves for measuring the conductivity $x_2$ in the alkaline range, contains the cation exchanger 32 and the conductivity measuring cell 34 as well as the valves 36 and 38.

The pH value is determined by measurement of the electric conductivity $x_1$ in the main loop 2 and by measurement of the conductivity $x_2$ in the parallel loop 30 as well as by measurement of the conductivity in $x_3$ in an additional parallel loop 40 by means of a conductivity measuring cell 44 which is arranged behind an anion exchanger 42 in series with a valve 46. The parallel loop 40 also contains a valve 48 for draining cooling water.

With a feed 50, an alkalizer or optionally, an acid in diluted form can be fed to the main loop 2 from a tank 52 via a dosing pump 54, and it can be determined first by the change of the conductivity $x_1$ of the water in which region the pH value of the water is. If an alkalizer is introduced into the main loop and the conductivity $x_1$ rises, a pH value in the basic region is present. If an acid is fed in and the conductivity $x_1$ of the water rises, the pH value is in the acid region. If the conductivity $x_1$ drops, the pH value is in the basic region.

If, for instance, the basic pH value region above 7 has been ascertained, the pH value is determined by measuring the conductivities $x_1$ and $x_2$ and derivation via the ion mobilities. In the acid pH value region below 7, the pH value is determined similarly by measuring the conductivities $x_1$ and $x_3$.

What is claimed is:

1. A method for determining a pH of acidic deionized water in a cooling water system for an electrical device comprising: diverting a portion of water through an anion exchanger loop in parallel with the system; measuring a first electric conductivity, $X_1$, of the water before its passage through the exchanger; measuring a second electric conductivity $X_4$ of the water after its passage through the exchanger; determining a temperature of the water; obtaining a mean cation mobility $1_k$, a mean anion mobility $1_a$, a hydroxide ion mobility $1_{OH}$, and a hydrogen ion mobility $1_H$ at said temperature by reference to a standard table of ion mobilities in aqueous solution as a function of temperature; and using a computing means to solve an equation for the pH, which equation is:

$$pH = + \log\left[\frac{1_a + 1_H}{1000}\right] - \log\left[X_1 - X_4\left(\frac{1_k + 1_a}{1_k + 1_{OH}}\right)\right]$$

and produce the pH value.

2. A method for determining a pH of basic deionized water in a cooling water system for an electrical device comprising diverting a portion of the water through a cation exchanger loop in parallel with the system; measuring a first electric conductivity $X_1$ of the water before the exchanger; measuring a second electric conductivity $X_2$ of the water after the exchanger; determining the water temperature; obtaining a mean cation mobility $1_k$, a mean anion mobility $1_a$, a hydroxide ion mobility $1_{OH}$, a hydrogen ion mobility $1_H$ and a water ionicity Kw at said temperature by reference to a standard table of ion mobilities in aqueous solution and a table of water ionicity as a function of temperature; and using a computing means to solve an equation for the pH, which equation is:

$$pH = -\log\left[\frac{(1_k + 1_{OH})}{1000} K_w\right] +$$

$$\log\left[X_1 - X_2\left(\frac{1_k + 1_a}{1_a + 1_H}\right)\right].$$

and produce the pH value.

3. A method for determining a pH of deionized water in a cooling water system for an electrical device comprising diverting a first portion of the water through a first cation exchanger loop in parallel with the system; diverting a second portion of the water through a second anion exchanger loop in parallel with the system; measuring a first electric conductivity $X_1$ of the water before its entry into the first and second loops; measuring a second electric conductivity $X_2$ of the water after it has passed through the cationic exchanger of the first loop; measuring a third electric conductivity $X_4$ of the water after it has passed through the anionic exchanger of the second loop; determining the water temperature; obtaining a mean cation mobility $1_k$, a mean anion mobility $1_a$, a hydroxide ion mobility $1_{OH}$, a hydrogen ion mobility $1_H$ and a water ionicity Kw at said temperature by reference to a standard table of ion mobilities in aqueous solution and a table of water ionicity as a function of temperature; and using a computing means to solve equations 1 and 2 for pH, $$pH = -\log\left[\frac{(1_k + 1_{OH})}{1000} K_w\right] + \log\left[X_1 - X_2\frac{(1_k + 1_a)}{(1_a + 1_H)}\right] \quad 1.$$

and $$pH = +\log\left[\frac{1_a + 1_H}{1000}\right] - \log\left[X_1 - X_4\left(\frac{1_k + 1_a}{1_k + 1_{OH}}\right)\right] \quad 2.$$

to produce the pH value, said equation 1 being used when the water is basic and said equation 2 being used when the water is acidic.

4. A method according to claim 3, further comprising determining the general basicity or acidity of the water by adding an amount of aqueous acid or aqueous base to the water which is sufficient to change the electrical conductivity in the system, and observing a rise or fall of the electric conductivity in the system; a rise in conductivity indicating the general acidity or basicity of the system is the same as that of the added acid or base and a fall in conductivity indicating the general acidity or basicity of the system is opposite from that of the added acid or base.

5. A method according to claim 1 wherein the cations are $Na^+$, $Cu^{+2}$, $FE^{+3}$, $Ni^{+2}$ and the anions are $HCO_3^-$, $CO_3^{-2}$, $SO_4^{-2}$ and $Cl^-$.

6. A method according to claim 2 wherein the cations are $Na^+$, $Cu^{+2}$, $Fe^{+3}$, $Ni^{+2}$ and the anions are $HCO_3^-$, $CO_3^{-2}$, $SO_4^{-2}$ and $Cl^-$.

7. A method according to claim 1 wherein the mean cation mobility at 298° K. is 52 mho cm$^2$, the mean anion mobility at 298° K. is 62 mho cm$^2$, the hydroxide ion mobility at 298° K. is 198.6 mho cm$^2$, the hydrogen ion mobility at 298° K. is 349.8 mho cm² and the equation is pH=−0.3853−log($X_1$−0.4549$X_4$).

8. A method according to claim 2 wherein the mean cation mobility at 298° K. is 52 mho cm², the mean anion mobility at 298° K. is 62 mho cm², the hydroxide ion mobility at 298° K. is 198.6 mho cm², the hydrogen ion mobility at 298° K. is 349.8 mho cm², the water ionicity at 298° K. is 1.008×10⁻¹⁴, and the equation is pH=14.60+log($X_1$−0.2768$X_2$).

* * * * *